United States Patent [19]

Grauert et al.

[11] Patent Number: 6,051,583
[45] Date of Patent: Apr. 18, 2000

[54] 2,3,3A,4,9,9A-HEXAHYDRO-8-HYDROXY-1H-BENZ[F]INDOLES, PROCESSES FOR PREPARING THEM AND THEIR USE AS PHARMACEUTICAL COMPOSITIONS

[75] Inventors: Matthias Grauert; Christoph Hoenke, both of Ingelheim am Rhein; Adrian Carter, Bingen am Rhein; Wolf-Dietrich Bechtel, Appenheim; Thomas Weiser, Nieder-Olm; Rainer Palluk, Bingen am Rhein; Uwe Pschorn, Mainz, all of Germany

[73] Assignee: Boehringer Ingelheim Pharma KG, Ingelheim, Germany

[21] Appl. No.: 09/365,064

[22] Filed: Jul. 30, 1999

[30] Foreign Application Priority Data

Jul. 31, 1998 [DE] Germany .................. 198 34 714

[51] Int. Cl.[7] .................. A61K 31/40; C07D 401/00; C07D 215/16; C07D 215/00; C07D 209/56
[52] U.S. Cl. .................. 514/314; 514/411; 514/311; 514/312; 514/313; 546/276.7; 546/153; 546/152; 546/155; 548/427
[58] Field of Search .................. 548/427; 546/276.7, 546/152; 514/411, 313, 339, 312, 311, 314

[56] References Cited

PUBLICATIONS

Lin, et al., J. Med. Chem., Centrally Acting Serotonergic and Dopaminergic Agents. 2. Synthesis and Structure–Activity Relationships of 2,3,3a,4,9,9a–Hexahydro–1 H–benz[f]indole Derivatives, 1993.

*Primary Examiner*—Zinna Northington Davis
*Assistant Examiner*—Binta Robinson
*Attorney, Agent, or Firm*—R. P. Raymond; M-E M. Devlin; A. R. Stempel

[57] ABSTRACT

The present invention relates to new substituted 2,3,3a,4,9,9a-hexahydro-8-hydroxy-1H-benz[f]indole derivatives, processes for preparing them and their use as pharmaceutical compositions. The indole derivatives according to the invention correspond to general formula 1:

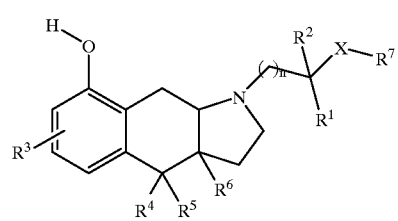

5 Claims, No Drawings

2,3,3A,4,9,9A-HEXAHYDRO-8-HYDROXY-1H-BENZ[F]INDOLES, PROCESSES FOR PREPARING THEM AND THEIR USE AS PHARMACEUTICAL COMPOSITIONS

The present invention relates to new substituted 2,3,3a, 4,9,9a-Hexahydro-8-hydroxy-1H-benz[f]indole derivatives, processes for preparing them and their use as pharmaceutical compositions. The indole derivatives according to the invention correspond to general formula 1:

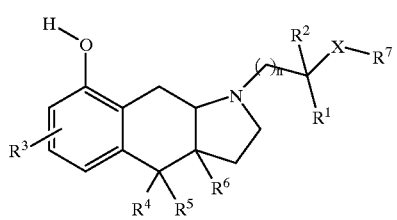

wherein

X denotes a single bond, —O—, $C_1$—$C_4$—alkyl, $C_1$—$C_3$—alkoxy, —O—$CH_2$—$CH_2$—O— or —O—$CH_2$—$CH_2$—NH—;

$R^1$ denotes hydrogen, methyl, ethyl or phenyl;

$R^2$ denotes hydrogen or methyl;

$R^3$ denotes hydrogen, F, Cl, Br, hydroxy or methoxy;

$R^4$ denotes hydrogen, methyl or ethyl;

$R^5$ denotes hydrogen, methyl or ethyl;

$R^6$ denotes hydrogen, methyl or ethyl;

$R^7$ denotes tert.-butyl, cylohexyl,

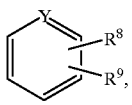 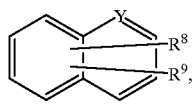 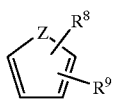

n denotes an integer 0 or 1;

Y denotes N or CH;

Z denotes O, NH or S;

$R^8$ denotes hydrogen, methyl, F, Cl, Br or methoxy;

$R^9$ denotes hydrogen, methyl, F, Cl, Br or methoxy.

The invention relates to the individual stereoisomers, the mixtures thereof and the corresponding physiologically suitable acid addition salts with inorganic or organic acids, such as HCl or HBr.

The enantiomerically pure compounds as well as the racemates are claimed. The trans-derivatives are preferred.

The compounds described are new. 1-($C_{1-8}$)Alkyl, ($C_{1-8}$) alkenyl- and. ($C_{1-8}$)alkinyl-2, 3,3a,4,9,9a-hexahydro-1H-benz[f] indoles are known from the prior art [WO-91/00856, C.-H. Lin et. al. J. Med. Chem. 1993, 36, 1069–1083]. These compounds are characterised as $D_2$ and 5-$HT_{1A}$ agonists and are claimed for a number of psychiatric diseases as well as metabolic disorders. By contrast, the aralkyl-, aryloxyalkyl-, alkoxy-, cycloalkylalkyl- and t-butylalkyl compounds claimed here are new. The 3a,4,4 trialkyl-substituted 2,3,3a, 4,9,9a-hexahydro-1H-benz[f]indoles are totally unknown, up till now.

Biological Properties

It is known from the prior art that cell damage and loss of function occurring as a result of hypoglycaemia, hypoxia, anoxia, trauma and ischaemia are partly based on an increased synaptic activity. A series of experiments have shown that hypoglycaemic and hypoxic conditions of this kind lead to massive depolarisation of the affected cells. As a result of this depolarisation, there is in turn a pathogenic increase in intracellular calcium and in the neuronal tissue there is additionally an increased release of excitatory amino acids. The voltage-dependent sodium channel has a key role in this cascade. Thus, by blocking it, it is possible to prevent the depolarisation of the cells, thereby reducing the influx of calcium through voltage-dependent calcium channels and in the neuronal tissue additionally through NMDA-receptor channels. Moreover, the reduced influx of sodium ions into the cell prevents the calcium/sodium exchanger from operating reciprocally and conveying calcium into the cell. The reduced influx of sodium ions into the cell also prevents the glutamate transporter from operating reciprocally and releasing glutamate [C. P. Taylor and B. S. Meldrum, Trends Pharmacol. Sci., 16, 309–316 (1995); J. Urenjak and T. P. Obrenovitch Am. Soc. Pharmacol. Rev. 48, 21–67 (1996)].

The compounds claimed are blockers of the voltage-dependent sodium channel. They are compounds which have Batrachotoxin (BTX) with a high affinity ($K_i<1000$ nM) and displace it competitively or non-competitively from the binding site on the sodium channel. Such substances show "use-dependency" in the blocking of the sodium channels, i.e. in order for the substances to bind to the sodium channel, the sodium channels first have to be activated. The maximum blockade of the sodium channels is only achieved after repeated stimulation of the sodium channels. Consequently, the substances preferentially bind to sodium channels which are repeatedly activated. As a result, the substances are in a position to act preferentially in those parts of the body which are pathologically overstimulated.

A suitable test system for detecting the sodium channel blocking effect is the BTX-binding to the sodium channel [S. W. Postma & W. A. Catterall, Mol. Pharmacol 25, 219–227 (1984)] as well as patch-clamp experiments, which show that the compounds according to the invention block the electrically stimulated sodium channel in a "use-dependent" manner [W. A. Catterall, Trends Pharmacol. Sci., 8, 57–65 (1987)].

Moreover, the compounds according to the invention have been shown to have a neuroprotective effect by blocking the release of glutamate induced by veratridine [S. Villauneva, P. Frenz, Y. Dragnic, F. Orrego, Brain Res. 461, 377–380 (1988)]. Veratridine is a toxin which permanently opens the sodium channel. As a result, there is an increased influx of sodium ions into the cell. By means of the cascade described above, this influx of sodium in the neuronal tissue leads to an increased release of glutamate. The compounds according to the invention antagonise this glutamate release.

The substances according to the invention were shown to have anticonvulsant properties by their protective effect against convulsions triggered by a maximum electric shock in mice [M. A. Rogawski & R. J. Porter, Pharmacol. Rev. 42, 223–286 (1990)], whilst neuroprotective properties were demonstrated by a protective effect in a rat-MCAO-model [U. Pschorn & A. J. Carter, J. Stroke Cerebrovascular Diseases, 6, 93–99 (1996)].

It has also been described that sodium channel blockers can be used for the treatment of cyclophrenia (manic depressive disease) [J. R. Calabrese, C. Bowden, M. J. Woyshville; in: Psychopharmacology: The Fourth Generation of Progress (Eds.: D. E. Bloom and D. J. Kupfer) 1099–1111. New York: Raven Press Ltd.]

Thus, it has been shown that 1,2,3,4,5,6-hexahydro-2,6-methano-3-benzazocin-10-oles of general Formula 1 can be used to treat diseases the causes of which are based on a functional disorder caused by overstimulation. These include diseases such as arrhythmia, spasm, cardiac and cerebral ischaemia and neurodegenerative diseases of various origins; these include, for example, epilepsy, hypoglycaemia, hypoxia, anoxia, brain trauma, cerebral oedema, stroke, perinatal asphyxia, amylotropic lateral sclerosis, Huntington's disease, Alzheimer's disease, Parkinson's disease, cyclophrenia, hypotonia, cardiac infarct, disorders of heart rhythm, Angina pectoris, pain of various forms and aetiology, such as nociceptor pain with excitation of pain receptors and transmission of the impulses to the CNS or neuropathic pain. Pain resulting from damage to the peripheral or central nervous system (e.g. after amputation, paraplegia, herpes or in diabetic polyneuropathy), pain caused by functional disorders, e.g. migraine caused by poor vascular regulation, back pain caused by poor physical posture—including psychosomatic processes such as sympathic activation in anxiety, muscle tensing in emotional stress. In connection with this, use as a local anaesthetic is possible, in particular.

EXAMPLES OF FORMULATIONS

1. Tablets

Composition:

| | |
|---|---|
| Active substance according to the invention | 20 parts by weight |
| Stearic acid | 6 parts by weight |
| Glucose | 474 parts by weight |

The ingredients are processed in the usual way to produce tablets weighing 500 mg. If desired, the content of active substance can be increased or reduced and the quantity of glucose reduced or increased accordingly.

2. Suppositories

Composition:

| | |
|---|---|
| Active substance according to the invention | 100 parts by weight |
| Powdered lactose | 45 parts by weight |
| Cocoa butter | 1555 parts by weight |

The ingredients are processed in the usual way to form suppositories weighing 1.7 g.

4. Solutions for infusion

The active substance according to the invention is added, in a pharmaceutically effective amount, e.g. to a physiologically acceptable starting solution such as 5% xylitol or mannitol which is suitable for infusion and known from the prior art using methods known from the prior art.

5. Powder for inhalation

Micronised powdered active substance (compound of Formula I; particle size about 0.5 to 7 μm) is packed into hard gelatine capsules in amounts of 5 mg, optionally with the addition of micronised lactose. The powder is inhaled using conventional inhalers, e.g. as in DE-A 33 45 722, to which reference is hereby made.

Method of Production

Key compounds in the synthesis are the nor-hexahydro-1H-benz[f]indoles 2a, shown here in the form of the corresponding (−)-enantiomer, as well as 3a and 3b.

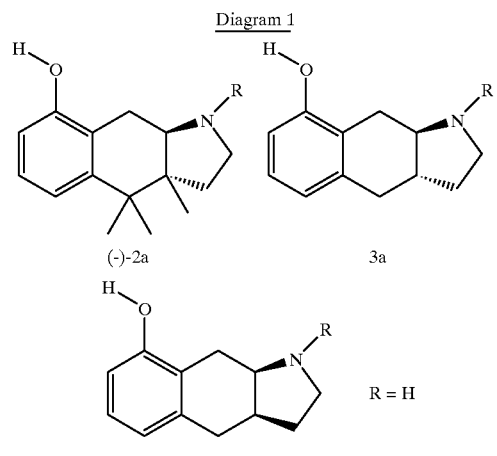

Diagram 1

Compound 2a was obtained by the method described in Diagram 2.

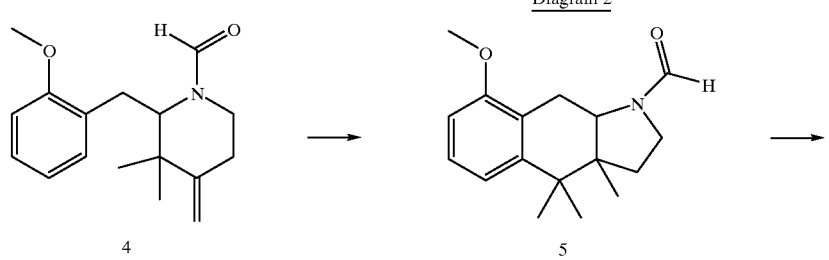

Diagram 2

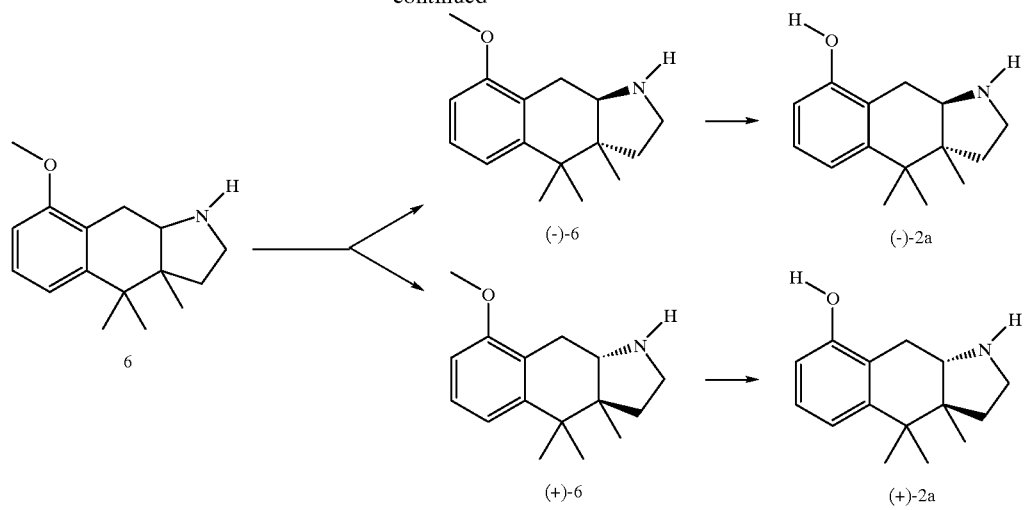
3a and 3b may be synthesised analogously to the process described in WO-A-91/00856. The method of synthesis is illustrated in Diagram 3.
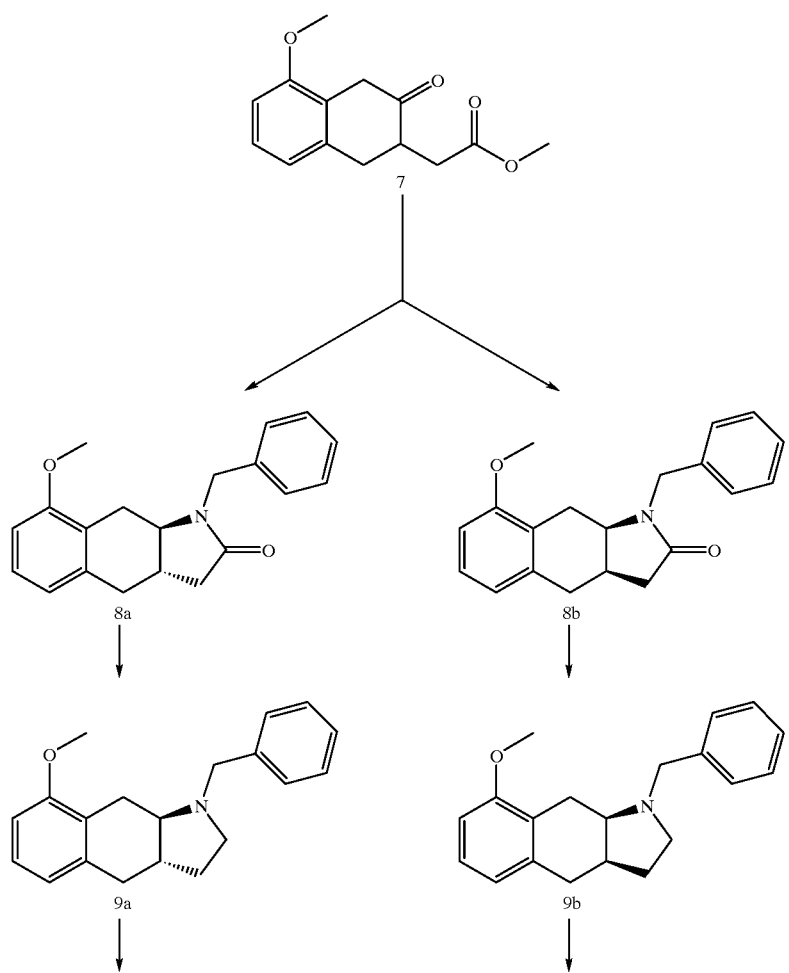

-continued

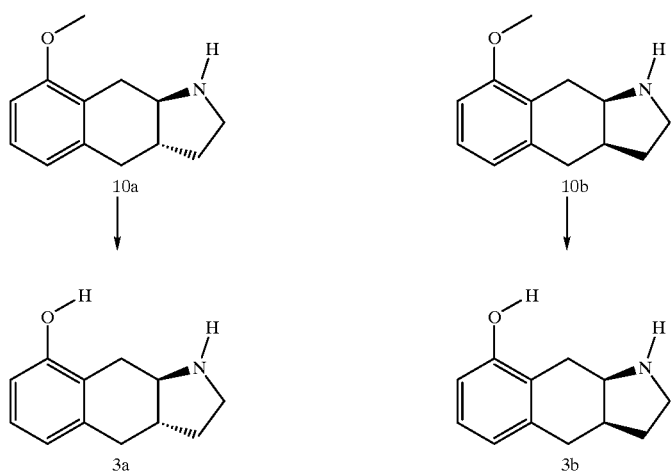

The N-substituent is introduced by reacting the key compounds 2a, 3a and 3b with acylating agents to obtain the intermediate compounds 11 and subsequently reducing them or by direct alkylation of the key compounds 2a or 3a or 3b with alkylating agents or by reacting with aldehydes to obtain 12 and subsequently reducing them. Diagram 4 shows these methods by way of example for key compound (−)-2a.

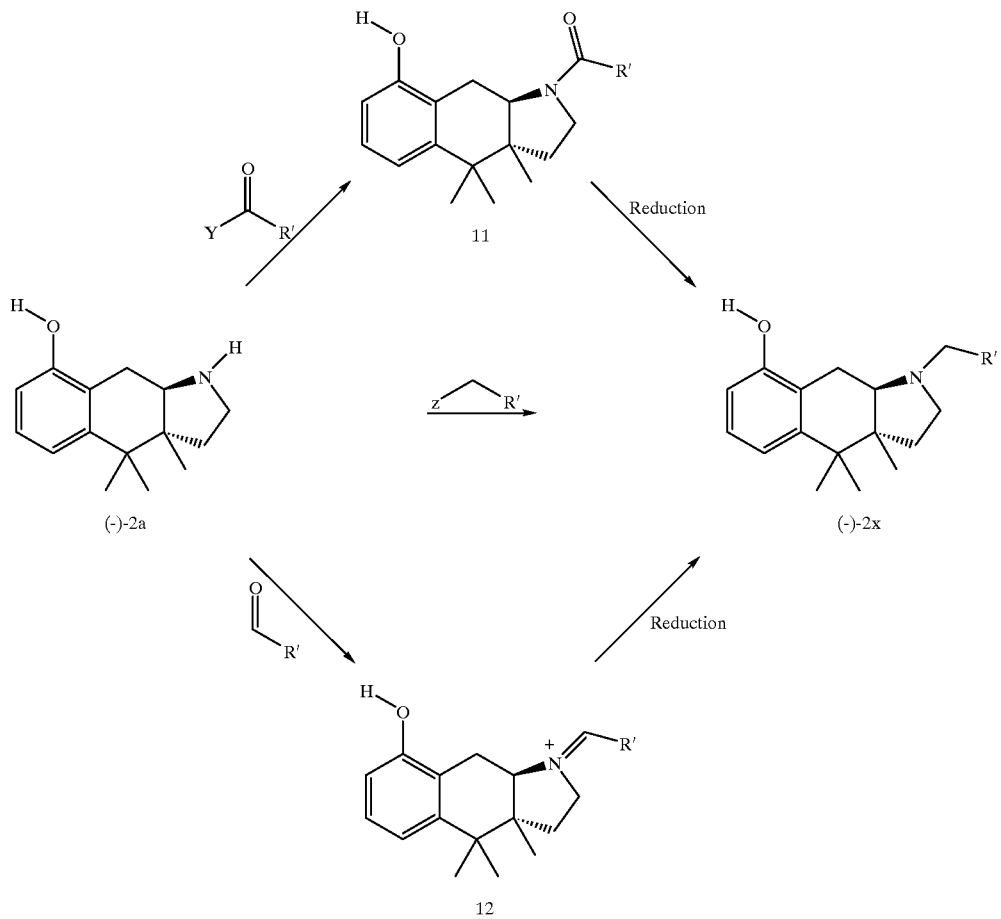

The compounds according to the invention can then be substituted regioselectively in the benzindole-partial structure. An Example is given for compound (–)-2b in Diagram 5.

Diagram 5

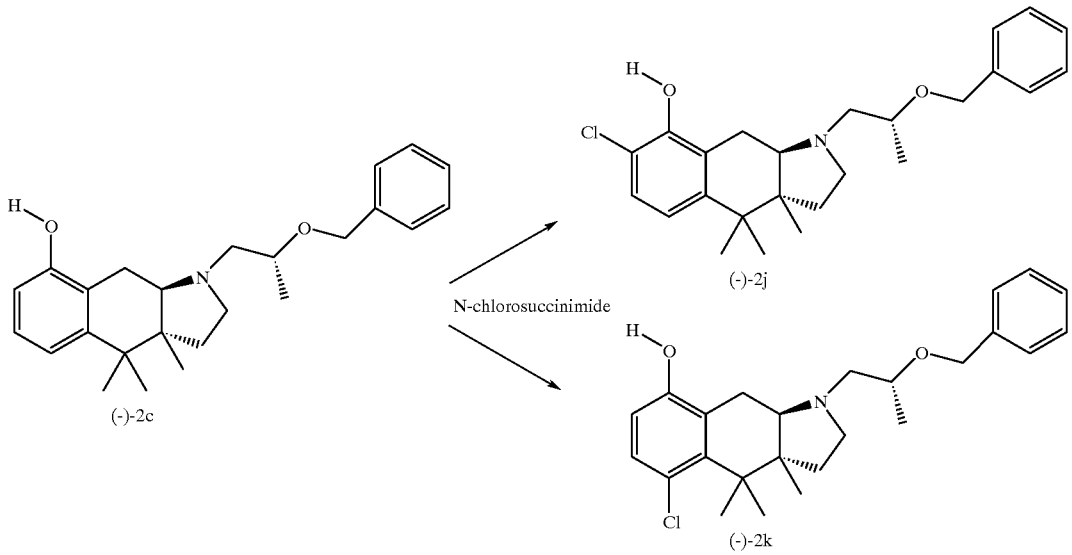

EXAMPLES

Example 1 trans-1-Formyl-8-methoxy-3a,4,4-trimethyl-2,3,3a,4,9,9a-hexahydro-1H-benz[f]indole (5)

To a suspension of 88.0 g (0.66 mol) of aluminium trichloride in 420 mL of absolute dichloromethane is added dropwise, at 0–5° C., a solution of 60.1 g (0.22 mol) of N-formyl-2-(2'-methoxyphenyl) methyl-3,3-dimethyl-4-methylene-piperidine (4) in 200 mL of dichloromethane within 2 h. The mixture is left to react for a further 3 h at 5° C. and then poured onto 800 mL of ice. The organic phase is separated off and the aqueous phase is extracted twice more with 250 mL of dichloromethane. The combined organic phases are dried over $MgSO_4$ and the solvent is eliminated in vacuo. The residue is chromatographed on silica gel (500 g silica gel, solvent: ethyl acetate). 36.0 g (60%) of trans-1-formyl-8-methoxy-3a, 4,4-trimethyl-2,3,3a,4,9,9a-hexahydro-1H-benz[f]indole (5) are obtained as an oil.

Example 2 trans-8-Methoxy-3a,4,4-trimethyl-2,3,3a,4,9,9a-hexahydro-1H-benz[f]indole (6)

9.6 g (35 mmol) of trans-1-formyl-8-methoxy-3a,4,4-trimethyl-2,3,3a,4,9,9a-hexahydro-1H-benz[f]indole (5) are dissolved in 75 mL of n-propanol and mixed with 25 mL of conc. hydrochloric acid and 15 mL of water. The mixture is refluxed for 12 h, the alcohol is eliminated in vacuo and diluted with 800 mL of water. The mixture is extracted once with 150 mL of ethyl acetate (discarded), the aqueous phase is made alkaline with sodium hydroxide and extracted three times with 200 mL ethyl acetate. The combined organic phases are dried over $MgSO_4$ and the solvent is eliminated in vacuo. 8.6 g (100%) of trans-8-methoxy-3a,4,4-trimethyl-2,3,3a,4,9,9a-hexahydro-1H-benz[f]indole (6) are obtained as an oil.

Example 3

(–)-1R-trans-8-Methoxy-3a,4,4-trimethyl-2,3,3a,4,9,9a-hexahydro-1H-benz[f]indole-malate ((–)6MA) and (+)-1S-trans-Methoxy-3a,4,4-trimethyl-2,3,3a,4,9,9a-hexahydro-1H-benz[f]indole-malate ((+)6MA)

8.6 g (35 mmol) of trans-8-methoxy-3a,4,4-trimethyl-2, 3,3a,4,9,9a-hexahydro-1H-benz[f]indole (6) are dissolved in 89 mL of methanol and combined with a solution of 8.5 g (63 mmol) of L-(–)-Äpfelsäure in 85 mL of methanol. The mixture is stirred for 1 h at RT, the crystals precipitated are suction filtered and recrystallised from 200 mL of methanol. 4.8 g (35%) of (–)-1R-trans-8-Methoxy-3a,4,4-trimethyl-2, 3,3a,4,9,9a-hexahydro-1H-benz[f]indole-malate ((–)6MA) are obtained, melting point: 214° C., $[\alpha]_D^{25}$=–42.5° (c=1, methanol).

The mother liquor is concentrated by evaporation, made alkaline with conc. ammonia and extracted twice with 200 mL ethyl acetate. The combined organic phases are dried over $MgSO_4$ and the solvent is eliminated in vacuo. Then (+)-1S-trans-methoxy-3a,4,4-trimethyl-2, 3,3a,4,9,9a-hexahydro-1H-benz[f]indole-malat ((+)6MA) is isolated using D-(+)-malic acid. Yield: 3.5 g (25%), melting point: 214° C., $[\alpha]_D^{25}$=+46.1° (c=1, methanol).

Example 4

(–)-1R-trans-8-Hydroxy-3a,4,4-trimethyl-2,3,3a,4,9,9a-hexahydro-1H-benz[f]indole-hydrobromide ((–)2aBr)

4.8 g (12.8 mmol) of (–)-1R-trans-8-methoxy-3a,4,4-trimethyl-2,3,3a,4,9,9a-hexahydro-1H-benz[f]indole-malate ((–)6MA) are first converted into the free base with conc. ammonia. Then 8 mL of water and 25 mL of 62% hydrobromic acid are added and the mixture is refluxed for 3 h. It is then concentrated by evaporation in vacuo and the residue is recrystallised from 30 mL of acetone. Yield: 3.9 g (98%), melting point: >250° C., $[\alpha]_D^{25}$ =–68.4° (c=1, methanol).

The following is obtained analogously to Example 4:

(+)-1R-trans-8-Hydroxy-3a,4,4-trimethyl-2,3,3a,4,9,9a-hexahydro-1H-benz[f]indole-hydrobromide ((+)2aBr)

19.3 g (51 mmol) of (+)-1R-trans-8-methoxy-3a,4,4-trimethyl-2,3,3a,4,9,9a-hexahydro-1H-benz[f]indole-malate ((+)6MA) are used. Yield: 14.4 (91%), melting point: >250° C., $[\alpha]_D^{25}$=+70.0° (c=1, methanol).

Example 5 trans-(±)-1-Benzyl-8-methoxy-2,3,3a,4,9,9a-hexahydro-1H-benz[f]indole-2-one ((8a) and cis-(±)-1-Benzyl-8-methoxy-2,3,3a,4,9,9a-hexahydro-1H-benz[f]indole-2-one (8b)

3.6 g (14.5 mmol) of methyl (±)-1,2,3,4-tetrahydro-5-methoxy-3-oxo-2-naphthalinoacetate (7) and 7.8 g (73 mmol) of benzylamine are dissolved in 50 mL of THF and 50 mL of methanol. The mixture is cooled to 0° C., acidified with glacial acetic acid to pH 4.5 and stirred for 30 min. Then 1.8 g (29 mmol) of sodium cyanoborohydride are added and the mixture is stirred for 3 days at ambient temperature gerührt. The reaction mixture is quenched with 20% sodium hydroxide solution and the organic solvent is eliminated in vacuo. Then it is extracted three times with 150 mL of dichloromethane, the combined organic phase is washed once with saturated sodium chloride solution, dried over MgSO$_4$ and the solvent is eliminated in vacuo. The residue is chromatographed on silica gel (about 1000 g silica gel, ethyl acetate/cyclohexane 1:1). 0.5 g (10%) 8a and 1.1 g (25%) 8b are obtained as an oil.

Example 6 cis-(±)-1-Benzyl-8-methoxy-2,3,3a,4,9,9a-hexahydro-1H-benz[f]indole ((9b)

0.51 g (13.4 mmol) of LiAlH$_4$ are placed in 5 mL of THF, cooled to 0° C. and a solution of 1.0 g (3.3 mmol) of cis-(±)-1-benzyl-8-methoxy-2,3,3a,4,9,9a-hexahydro-1H-benz[f]indol-2-one ((8b) in 20 mL of THF is added dropwise. Then the mixture is refluxed for 5 h, cooled to ambient temperature and 100 mL of saturated sodium sulphate solution are added. The mixture is extracted three times with 100 mL ethyl acetate, the combined organic phase is dried over MgSO$_4$ and the solvent is eliminated in vacuo. The residue is suspended in 15 mL methanol, the insoluble matter is removed by suction filtering and the solvent is eliminated in vacuo. 0.5 g (52%) 9b are obtained as an oil.

The following is obtained analogously to Example 6:

trans-(±)-1-Benzyl-8-methoxy-2,3,3a,4,9,9a-hexahydro-1H-benz[f]indole (9a)

0.21 g (5.5 mmol) of LiAlH$_4$ and 0.5 g (1.6 mmol) of trans-(±)-1-benzyl-8-methoxy-2, 3,3a,4,9,9a-hexahydro-1H-benz[f]indol-2-one (8a) are used. Yield: 0.4 g (85%).

Example 7 cis-(±)-8-methoxy-2,3,3a,4,9,9a-hexahydro-1H-benz[f]indole (10b)

1.7 g (5.8 mmol) of cis-(±)-1-benzyl-8-methoxy-2,3,3a,4,9,9a-hexahydro-1H-benz[f]indole (9b) are dissolved in 35 mL of methanol and hydrogenated at 20° C. and 5 bars of hydrogen pressure on 0.2 g of Pd/C (10%). After 5 h the mixture is filtered over silica gel and the solvent is eliminated in vacuo. 1.2 g (100%) 10b are obtained as an oil.

The following is prepared analogously to Example 7:

trans-(±)-8-methoxy-2,3,3a,4,9,9a-hexahydro-1H-benz[f]indole (10a)

0.47 g (1.6 mmol) of trans-(±)-1-benzyl-8-methoxy-2,3,3a,4,9,9a-hexahydro-1H-benz[f]indole (9a) are used. 0.32 g (100%) of 1 are obtained as an oil.

Example 8 cis-(±)-8-Hydroxy-2,3,3a,4,9,9a-hexahydro-1H-benz[f]indole-hydrobromide (3bBr)

0.55 g (2.7 mmol) of cis-(±)-8-methoxy-2,3,3a,4,9,9a-hexahydro-1H-benz[f]indole (10b) are added to 6 mL of water and 12 mL of conc. hydrobromic acid and refluxed for 20 h . Then the mixture is concentrated by evaporation in vacuo, the residue is taken up again in 10 mL of ethanol and the solvent is eliminated again in vacuo. 0.69 g (95%) of the desired product are obtained as the hydrobromide.

The following is prepared analogously to Example 8:

trans-(±)-8-Hydroxy-2,3,3a,4,9,9a-hexahydro-1H-benz[f]indole-hydrobromide (3aBr)

0.32 g (1.6 mmol) of trans-(±)-8-methoxy-2,3,3a,4,9,9a-hexahydro-1H-benz[f]indole (10a) are used. Yield: 0.41 g (95%).

Example 9

(–)-(1R,2'R)-trans-1-(2'-Benzyloxy)propyl-8-hydroxy-3a,4,4-trimethyl-2,3,3a,4,9,9a-hexahydro-1H-benz[f]indole-hydrochloride ((–)2bHCl)

4.65 g (15 mmol) of (–)-1R-trans-hydroxy-3a,4,4-trimethyl-2,3,3a,4,9,9a-hexahydro-1H-benz[f]indole-hydrobromide ((–)2aHBr) and 5.0 g (39 mmol) of triethylamine are dissolved in 35 mL of dichloromethane and after 30 min. a solution of 3.6 g (18 mmol) of (+)-R-2-benzyloxypropionic acid chloride in 10 mL of dichloromethane is added dropwise. The mixture is stirred for a further 2 h at ambient temperature, combined with 20 mL of 2 N hydrochloric acid and the organic phase is separated off. The organic phase is dried over MgSO$_4$, the solvent is eliminated in vacuo and the residue is taken up in 60 mL of tetrahydrofuran. To this solution are added 1.9 g (50 mmol) of LiAlH4 while the temperature rises to 35° C. The solution is left to react for 1 h, mixed with 20 mL of 40% ammonium tartrate solution, the organic phase is separated off and extracted twice with 100 mL of ethyl acetate. The combined organic phases are dried over MgSO$_4$ and the solvent is eliminated in vacuo. The residue is taken up in 50 mL of acetone and the hydrochloride is precipitated with ethereal hydrochloric acid. The crystals are separated off and washed with acetone. Yield: 2.8 g (45%), melting point: 236° C., $[\alpha]_D^{25}$=(–) 124.3° (C=1 in methanol).

The following are prepared analogously to Example 9:

(–)-(1R,2'S)-trans-1-(2'-Benzyloxy)propyl-8-hydroxy-3a,4,4-trimethyl-2,3,3a,4,9,9a-hexahydro-1H-benz[f]indole-hydrochloride ((–)2cCl) 5.9 g (19 mmol) of (–)-1R -trans-hydroxy-3a,4,4-trimethyl-2,3,3a,4,9,9a-hexahydro-1H-benz[f]indole-hydrobromide ((–)2aHBr) and 3.8 g (19 mmol) of (–)-S-2-benzyloxypropionic acid chloride are used. Yield: 3.2 g (40%), melting point: >250° C., $[\alpha]_D^{25}$ =(–) 11.9° (C=1 in methanol).

(+)-(1S,2'S)-trans-1-(2'-Benzyloxy)propyl-8-hydroxy-3a,4,4-trimethyl-2,3,3a,4,9,9a-hexahydro-1H-benz[f]indole-hydrochloride ((+)2bHCl)

1.6 g (5 mmol) of (+)-1R-trans-hydroxy-3a,4,4-trimethyl-2,3,3a,4,9,9a-hexahydro-1H-benz[f]indole-hydrobromide ((+)2aBr) and 1.0 g (5.0 mmol) of (–)-S-2-benzyloxypropionic acid chloride are used. Yield: 1.3 g (63%), melting point: 236° C., $[\alpha]_D^{25}$=(+) 124.8° (C=1 in methanol).

(+)-(1S,2'R)-trans-1-(2'-Benzyloxy)propyl-8-hydroxy-3a,4,4-trimethyl-2,3,3a,4,9,9a-hexahydro-1H-benz[f]indole-hydrochloride ((+)2cHCl)

1.6 g (5 mmol) of (+)-1R-trans-hydroxy-3a,4,4-trimethyl-2,3,3a,4,9,9a-hexahydro-1H-benz[f]indole-hydrobromide ((+)2aBr) and 1.0 g (5 mmol) of (+)-R-2-benzyloxypropionic acid chloride are used. Yield: 1.0 g (48%), melting point: >250° C., $[\alpha]_D^{25}$=(+) 12.7° (C=1 in methanol).

(+)-(1S,2'S)-trans-8-Hydroxy-1-(2'-methoxy-2"phenyl)ethyl -3a,4,4-trimethyl-2, 3,3a,4,9 ,9a-hexahydro-1H-benz[f]indole-hydrochloride ((+)2dHCl)

1.6 g (5 mmol) of (+)-1R-trans-hydroxy-3a,4,4-trimethyl-2,3,3a,4,9,9a-hexahydro-1H-benz[f]indole-hydrobromide ((+)2aBr) and 0.9 g (5 mmol) of (+)-S-2-methoxyphenylacetic acid chloride are used. Yield: 0.9 g (45%), melting point: >250° C., $[\alpha]_D^{25}$=(+) 174.2° (C=1 in methanol). (−)-(1R)-trans-8-Hydroxy-1-(2'-phenoxy)ethyl-3a,4,4-trimethyl-2,3,3a,4,9,9a-hexahydro-1H-benz[f]indole-hydrochloride ((−)2eHCl)

1.6 g (5 mmol) of (−)-1R-trans-hydroxy-3a,4,4-trimethyl-2,3,3a,4,9,9a-hexahydro-1H-benz[f]indole-hydrobromide ((−)2aHBr) and 0.8 g (6 mmol) of 2-phenoxyacetic acid chloride are used. Yield: 0.9 g (46%), melting point: 248° C., $[\alpha]_D^{25}$=(−)69.3° (C=1 in methanol).

(+)-(1S)-trans-8-Hydroxy-1-(2'-phenoxy)ethyl-3a,4,4-trimethyl-2,3,3a,4,9,9a-hexahydro-1H-benz[f]indole-hydrochloride ((+)2eHCl) 1.6 g (5 mmol) of (+)-1S-trans-hydroxy-3a,4,4-trimethyl-2,3,3a,4,9,9a-hexahydro-1H-benz[f]indole-hydrobromide ((+)2aHBr) and 0.8 g (6 mmol) of 2-phenoxyacetic acid chloride are used. Yield: 1.2 g (62%), melting point: 254° C., $[\alpha]_D^{25}$=(+) 71.5° (C=1 in methanol).

trans-(±)-8-Hydroxy-1-(2'-(2"-phenoxy)ethoxy)ethyl-2,3,3a,4,9,9a-hexahydro-1H-benz[f]indole-oxalate (3eOX)

0.2 g (0.74 mmol) of trans-(±)-8-Hydroxy-2,3,3a,4,9,9a-hexahydro-1H-benz[f]indole-hydrobromide (3aBr) and 0.2 g (0.93 mmol) of 2-(2'-phenoxy)ethoxy)acetic acid chloride are used. The base is converted into the oxalate with ethereal oxalic acid. Yield: 0.16 g (55%), melting point: 181° C.

cis-(±)-8-Hydroxy-1-(2'-(2"-phenoxy)ethoxy)ethyl-2,3,3a,4,9,9a-hexahydro-1H-benz[f]indole-oxalate (3fOX)

0.63 g (2.3 mmol) of cis-(±)-8-hydroxy-2,3,3a,4,9,9a-hexahydro-1H-benz[f]indole-hydrobromide (3bHBr) and 0.5 g (2.6 mmol) of 2-(2'-phenoxy)ethoxy)acetic acid chloride are used. The base is converted into the oxalate with ethereal oxalic acid. Yield: 0.3 g (33%), melting point: 176° C.

Example 10

(+)-(1S,2'S)-trans-1-(2'-(2",6"-difluorobenzyloxy)propyl-8-hydroxy-3a,4,4-trimethyl-2, 3,3a,4,9,9a-hexahydro-1H-benz[f]indole-hydrochloride ((+)2fHCl)

1,46 g (4.7 mmol) of (+)-1R-trans-hydroxy-3a,4,4-trimethyl-2,3,3a,4,9,9a-hexahydro-1H-benz[f]indole-hydrobromide ((+)2aHBr) and 1.0 g (4.6 mmol) of (−)-S-2-(2',6'-difluorobenzyloxy) propionic acid are dissolved in a mixture of 50 mL of tetrahydrofuran and 50 mL of dichloromethane and mixed with 0.8 g of benzotriazole and 4 mL of ethyldiisopropylamine. Then 0.9 g of TBTU are added and stirred for 2 h at RT. Then the solvent is eliminated in vacuo, the residue is taken up in 100 mL of ethyl acetate and extracted once with 100 mL of saturated potassium hydrogen carbonate solution and 100 mL of 1 N hydrochloric acid solution. The organic phase is dried over MgSO$_4$ and the solvent is eliminated in vacuo. The residue is taken up in 20 mL of THF and mixed with 0.5 g (13 mmol) of LiAlH$_4$. The mixture is reacted for 1 h at 50° C., 50 mL of 40% of ammonium tartrate solution are added, the organic phase is separated off and extracted twice with 100 mL ethyl acetate. The combined organic phases are dried over MgSO$_4$ and the solvent is eliminated in vacuo. The residue is taken up in 50 mL of acetone and the hydrochloride is precipitated with ethereal hydrochloric acid. The crystals are separated off and washed with acetone. Yield: 1.3 g (63%), melting point: 242° C., $[\alpha]_D^{25}$=(+) 116.4° (C=1 in methanol).

The following are prepared analogously to Example 10:

(−)-(1R,2'S)-trans-1-(2'-(2",6"-difluorobenzyloxy)propyl-8-hydroxy-3a,4,4-trimethyl-2, 3,3a,4,9,9a-hexahydro-1H-benz[f]indole-hydrochloride ((+)2gCl7HCl)

1.5 g (4.7 mmol) of (−)-1R-trans-hydroxy-3a,4,4-trimethyl-2,3,3a,4,9,ga-hexahydro-1H-benz[f]indole-hydrobromide ((−)2aBr) and 1.0 g (4.6 mmol) of (−)-S-2-(2',6'-difluorobenzyloxy) propionic acid are used. Yield: 1.3 g (63%), melting point: 260° C., $[\alpha]_D^{25}$=(−) 33.8° (C=1 in methanol). (1RS,2'S)-trans-1-(2'-Benzyloxy)propyl-8-hydroxy-2,3,3a,4,9,9a-hexahydro-1H-benz[f]indole-oxalat (3cOX) 0.2 g (0.74 mmol) of trans-(±)-8-hydroxy-2,3,3a,4,9,9a-hexahydro-1H-benz[f]indole-hydrobromide (3aBr) and 0.13 g (0.74 mmol) of (−)-S-(2-(benzyloxy)propionic acid are used. The base is converted into the oxalate with ethereal oxalic acid. Yield: 0.13 g (46%), melting point: 193° C.

(1RS,2'S)-cis-1-(2'-Benzyloxy)propyl-8-hydroxy-2,3,3a,4,9,9a-hexahydro-1H-benz[f]indole-oxalat (3dOX)

0.46 g (1.7 mmol) of cis-(±)-8-hydroxy-2,3,3a,4,9,9a-hexahydro-1H-benz[f]indole-hydrobromide ((3bHBr) and 0.31 g (1.7 mmol) of (−)-S-(2-(benzyloxy)propionic acid are used. The base is converted into the oxalate with ethereal oxalic acid. Yield: 0.25 g (38%).

Example 11

(−)-(1R)-trans-8-Hydroxy-1-(2'-(2"-phenoxy)ethoxy)ethyl-3a,4,4-trimethyl-2,3,3a,4,9,9a-hexahydro-1H-benz[f]indole-hydrochloride ((−)2hHCl)

3.1 g (10 mmol) of (−)-1R-trans-hydroxy-3a,4,4-trimethyl-2,3,3a,4,9,9a-hexahydro-1H-benz[f]indole-hydrobromide ((−)2aBr) and 2.2 g (11 mmol) of 2-(2-phenoxy)ethoxy-ethylcholoride are dissolved in 50 mL of DMF (dimethylformamide), a catalytic amount of Kl and 3 g of sodium carbonate are added. The mixture is refluxed for 57 h. Then the inorganic salts are separated off by suction filtering and the solvent is eliminated in vacuo. The residue is taken up in 100 mL of water, extracted three times with 100 mL ethyl acetate and the combined organic extracts are washed once again with 50 mL of water, dried over MgSO$_4$ and the solvent is eliminated in vacuo. The residue is filtered over a short silica gel column (25 g silica gel, 300 mL ethyl acetate), dissolved in acetone and the hydrochloride is precipitated with ethereal hydrochloric acid. Yield: 3.3 g (76%), melting point: 186° C., $[\alpha]_D^{25}$=(−) 72.1° (c=1 in methanol).

The following are prepared analogously to Example 11:

(+)-(1S)-trans-8-Hydroxy-1-(2'-(2"-phenoxy)ethoxy)ethyl-3a,4,4-trimethyl-2,3,3a,4,9,9a-hexahydro-1H-benz[f]indole-hydrochloride ((+)2hHCl)

3.1 g (10 mmol) of (+)-1R-trans-hydroxy-3a,4,4-trimethyl-2,3,3a,4,9,9a-hexahydro-1H-benz[f]indole-hydrobromide ((+)2aHBr) and 2.2 g (11 mmol) of 2-(2-phenoxy)ethoxy-ethylchloride are used. Yield: 3.2 g (74%), melting point: 186° C., $[\alpha]_D^{25}$=(+) 71.4° (c=1 in methanol).

(+)-(1S)-trans-8-Hydroxy-1-(2'-(2"-(8"-quinolinoxy)ethoxy)ethyl-3a,4,4-trimethyl-2, 3,3a,4,9 ,9a-hexahydro-1H-benz[f]indole-hydrochloride ((+)2iHCl) 1.25 g (4 mmol) of (+)-1R-trans-hydroxy-3a,4,4-trimethyl-2,3,3a,4,9,9a- hexahydro-1H-benz[f]indole-hydrobromide ((+)2aHBr) and 1.2 g (4 mmol) of 2-(2'-(8''-quinolinoxy) ethoxy) ethylchloride are used. Yield: 0.8 g (40%), melting point: 167° C., $[\alpha]_D^{25}$=(+) 44.2° (c=1 in methanol).

(−)-(1R)-trans-8-Hydroxy-1-(2'-(2''-(8''-quinolinoxy) ethoxy)ethyl-3a,4,4-trimethyl-2, 3,3a,4,9 ,9a-hexahydro-1H-benz[f]indole ((−)2i)

1.25 g (4 mmol) of (−)-1R-trans-hydroxy-3a,4,4-trimethyl-2,3,3a,4,9,9a-hexahydro-1H-benz[f]indole-hydrobromide ((−)2aBr) and 1.2 g (4 mmol) of 2-(2'-(8''-quinolinoxy) ethoxy)ethylchloride are used. The free base is recrystallised from ethyl acetate/cyclohexane. Yield: 0.7 g (39%), melting point: 163° C., $[\alpha]_D^{25}$=(−) 84.8° (c=1 in methanol).

Example 12

(+)-(1S)-trans-1-(3-Furanyl)methyl-8-hydroxy-3a,4,4-trimethyl-2,3,3a,4,9,9a-hexahydro-1H-benz[f]indole-hydrochloride ((+)2jHCl)

0.93 g (4 mmol) of (+)-1R-trans-hydroxy-3a,4,4-trimethyl-2,3,3a,4,9,9a-hexahydro-1H-benz[f]indole ((+)2a) and 0.6 mL (7.2 mmol) of 3-furanylaldehyde are dissolved in 10 mL of methanol, combined with molecular sieve and stirred for 2 h at RT. Then the molecular sieve is filtered off and the filtrate is mixed with 0.31 g (5 mmol) of sodium cyanoborohydride and 1.2 mL of glacial acetic acid. The mixture is left to stand overnight, 20 mL of 4 N hydrochloric acid are added and the resulting mixture is concentrated by evaporation in vacuo. The residue is dissolved in acetone and the hydrochloride is precipitated with ethereal hydrochloric acid. Yield: 0.7 g (50%), melting point: >250° C., $[\alpha]_D^{25}$=(+) 99.8° (C=1 in methanol).

The following is prepared analogously to Example 12:

(−)-(1R)-trans-1-(3-furanyl)methyl-8-hydroxy-3a,4,4-trimethyl-2,3,3a,4,9,9a-hexahydro-1H-benz[f]indole-hydrochloride ((−)2jHCl)

0.93 g (4 mmol) of (−)-1R-trans-hydroxy-3a,4,4-trimethyl-2,3,3a,4,9,9a-hexahydro-1H-benz[f]indole ((−)2a) and 0.6 mL (7.2 mmol) of 3-furanylaldehyde are used. Yield: 0.7 g (50%), melting point: >250° C., $[\alpha]_D^{25}$=(−) 102.3° (C=1 in methanol).

Example 13

(−)-(1R,2'S)-trans-1-(2'-benzyloxy)propyl-7-chloro-8-hydroxy-3a,4,4-trimethyl-2, 3,3a,4,9,9a-hexahydro-1H-benz[f]indole-hydrochloride ((−)2jHCl) and (−)-(1R,2'S)-trans-1-(2'-benzyloxy) propyl-5-chloro-8-hydroxy-3a,4,4-trimethyl-2,3,3a,4,9,9a-hexahydro-1H-benz[f]indole-hydrochloride ((−)2kHCl) 1.0 g (2.4 mmol) of (−)-(1R,2'S)-trans-1-(2'-benzyloxy)propyl-8-hydroxy-3a,4,4-trimethyl-2, 3,3a,4,9,9a-hexahydro-1H-benz[f]indole-hydrochloride ((−)2cHCl) and 0.3 g (2.5 mmol) of N-chlorosuccinimide are suspended in 20 mL of glacial acetic acid and stirred for 24 h at RT during which time the suspension goes into solution. Then the mixture is concentrated by evaporation in vacuo, the residue is combined with 100 mL of ice-cold 2 N sodium hydroxide solution and extracted three times with 100 mL of ethyl acetate. The combined organic phases are dried over MgSO$_4$ and the solvent is eliminated in vacuo. Then the residue is chromatographed on aluminium oxide (dichloromethanel methanol 19: 1). The appropriate fractions are concentrated by evaporation and the residue is dissolved in 15 mL acetone and the hydrochloride is precipitated with ethereal hydrochloric acid. 0.4 g (37%) (−)-2jHCl, melting point: 218° C., $[\alpha]D^{25}$=(−) 12.3° (C=1 in methanol) and 0.44 g (41%) (−)-2kHCl, melting point: >250° C., $[\alpha]_D^{25}$=(−) 14.4° (C=1 in methanol) are obtained.

The following is prepared analogously to Example 13:

(−)-(1R,2'R)-trans-1-(2'-benzyloxy)propyl-7-chloro-8-hydroxy-3a,4,4-trimethyl-2, 3,3a,4,9,9a-hexahydro-1H-benz[f]indole-hydrochloride ((−)2lHCl) and (−)-(1R,2'R)-trans-1-(2'-benzyloxy) propyl-5-chloro-8-hydroxy-3a,4,4-trimethyl-2,3,3a,4,9,9a-hexahydro-1H-benz[f]indole-hydrochloride ((−)2mHCl)

0.42 g (1.0 mmol) of (−)-(1R,2'S)-trans-1-(2'-benzyloxy) propyl-8-hydroxy-3a,4,4-trimethyl-2, 3,3a,4,9,9a-hexahydro-1H-benz[f]indole-hydrochloride ((−)2cCl) and 0.13 g (1.1 mmol) of N-chlorosuccinimide are used. 0.1 g (22%) (−)-2lHCl, melting point: 234° C., $[\alpha]_D^{25}$=(−) 117.5° (C=1 in methanol) and 0.17 g (38%) (−)-2mHCl, melting point: 252° C., $[\alpha]_D^{25}$=(−) 126.7° (C=1 in methanol) are obtained.

What is claimed is:

1. An indole compound of formula 1:

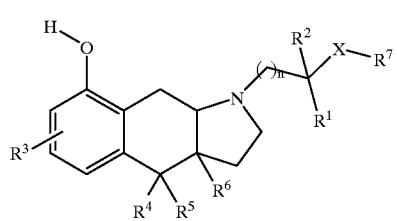

wherein

X may denote a single bond, —O—, $C_1$—$C_4$—alkyl, $C_1$—$C_3$—alkoxy, —O—$CH_2$—$CH_2$—O— or —O—$CH_2$—$CH_2$—NH—;

$R^1$ may denote hydrogen, methyl, ethyl or phenyl;

$R^2$ may denote hydrogen or methyl;

$R^3$ may denote hydrogen, F, Cl, Br, hydroxy or methoxy;

$R^4$ may denote hydrogen, methyl or ethyl;

$R^5$ may denote hydrogen, methyl or ethyl;

$R^6$ may denote hydrogen, methyl or ethyl;

$R^7$ may denote tert,-butyl, cyclohexyl,

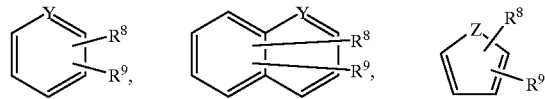

n may denote an integer 0 or 1;

Y may denote N or CH;

Z may denote O, NH or S;

$R^8$ may denote hydrogen, methyl, F, Cl, Br or methoxy;

$R^9$ may denote hydrogen, methyl, F, Cl, Br or methoxy;

an individual stereoisomer thereof or a mixture of stereoisomers, or an acid addition salt thereof with an inorganic or organic acid.

2. The indole compound according to claim 1, wherein that it is in trans form.

3. A pharmaceutical composition comprising an indole compound according to claim 1 and together an adjuvant or carrier.

4. A method of treating disease in a warm-blooded animal which disease involves release of glutamate which method comprises administering to the warm-blooded animal a therapeutically effective amount of an indole compound according to claim 1.

5. A method for treating disease in a warm-blooded animal which disease involves activation of sodium channels which method comprises administering to the warm-blooded animal a therapeutically effective amount of an indole compound according to claim 1.

* * * * *